United States Patent
Taber et al.

(10) Patent No.: US 12,156,805 B2
(45) Date of Patent: *Dec. 3, 2024

(54) HYDRAULIC DELIVERY OF SURGICAL IMPLANTS

(71) Applicant: Alcon Inc., Fribourg (CH)

(72) Inventors: Todd Taber, Keller, TX (US); Kathryn Jensen, Sugar Land, TX (US); Michael Piazza, Crowley, TX (US); Jestwin Edwin Lee, IV, Grandview, TX (US); Saumya Dilip Yadav, Arlington, TX (US); Pradeep Shivalingappa Magadum, Arlington, TX (US); Austin Xavier Rodeheaver, Arlington, TX (US)

(73) Assignee: ALCON INC., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,300

(22) Filed: Jun. 26, 2023

(65) Prior Publication Data

US 2023/0404744 A1    Dec. 21, 2023

Related U.S. Application Data

(63) Continuation of application No. 17/335,254, filed on Jun. 1, 2021, now Pat. No. 11,925,548.

(60) Provisional application No. 63/033,258, filed on Jun. 2, 2020.

(51) Int. Cl.
*A61F 2/16*    (2006.01)

(52) U.S. Cl.
CPC ............ *A61F 2/167* (2013.01); *A61F 2/1675* (2013.01); *A61F 2/1678* (2013.01); *A61F 2230/0093* (2013.01); *A61F 2250/0069* (2013.01)

(58) Field of Classification Search
CPC ...... A61F 2/148; A61F 2/167; A61F 17/3468; A61F 9/00; A61F 9/0008; A61F 9/0017; A61F 9/0026; A61F 9/0061; A61F 9/007
See application file for complete search history.

(56) References Cited

U.S. PATENT DOCUMENTS

| | | |
|---|---|---|
| 7,156,854 B2 | 1/2007 | Brown et al. |
| 8,308,736 B2 | 11/2012 | Boukhny et al. |
| 8,308,799 B2 | 11/2012 | Chen et al. |
| 8,377,076 B2 | 2/2013 | Downer et al. |
| 8,956,408 B2 | 2/2015 | Smiley et al. |
| 8,968,396 B2 | 3/2015 | Matthews et al. |
| 9,480,555 B2 | 11/2016 | Downer et al. |
| 9,610,155 B2 | 4/2017 | Matthews et al. |
| 9,693,858 B2 | 7/2017 | Hildebrand et al. |

(Continued)

FOREIGN PATENT DOCUMENTS

| | | |
|---|---|---|
| EP | 1800623 A1 | 6/2007 |
| EP | 1857076 B1 | 7/2010 |

(Continued)

*Primary Examiner* — Sarah W Aleman

(57) ABSTRACT

An apparatus for delivering an implant to an eye using hydraulic fluid flow or pressure. An implant may be stored, advanced, and delivered to an eye using hydraulic fluid stored in a sterile container through a hollow advancement plunger. The plunger may rigidly advance the implant to a sealed position in a first phase, and then the implant may be advanced into the eye via hydraulic pressure or fluid flow in a second phase.

16 Claims, 12 Drawing Sheets

(56) References Cited

U.S. PATENT DOCUMENTS

| | | |
|---|---|---|
| 9,855,139 B2 * | 1/2018 | Matthews ............ A61F 2/1675 |
| 10,172,706 B2 | 1/2019 | Auld et al. |
| 10,195,020 B2 | 2/2019 | Matthews et al. |
| 10,568,735 B2 | 2/2020 | Brown et al. |
| 10,588,780 B2 | 3/2020 | Van Noy et al. |
| 11,039,953 B2 | 6/2021 | Balachandran |
| 12,004,944 B2 | 6/2024 | Weston |
| 2008/0097460 A1 | 4/2008 | Boukhny et al. |
| 2010/0057093 A1 | 3/2010 | Ide et al. |
| 2011/0265779 A1 | 11/2011 | Vandrak et al. |
| 2012/0022548 A1 | 1/2012 | Zacharias |
| 2013/0197532 A1 | 8/2013 | Boukhny et al. |
| 2013/0253527 A1 * | 9/2013 | Schneider ............ A61F 9/007 606/107 |
| 2014/0012277 A1 | 1/2014 | Matthews et al. |
| 2014/0276898 A1 * | 9/2014 | Novak ............ A61F 2/167 606/107 |
| 2016/0087460 A1 | 3/2016 | Rich et al. |
| 2017/0007237 A1 | 1/2017 | Yates et al. |
| 2017/0027686 A1 | 2/2017 | Nagasaka et al. |
| 2018/0049866 A1 | 2/2018 | Fayyaz et al. |
| 2018/0200046 A1 | 7/2018 | Brown et al. |
| 2020/0179101 A1 | 6/2020 | Flowers et al. |
| 2020/0179102 A1 | 6/2020 | Chen et al. |
| 2020/0179103 A1 | 6/2020 | Auld et al. |
| 2020/0188089 A1 | 6/2020 | Auld et al. |
| 2020/0197170 A1 | 6/2020 | Auld et al. |
| 2021/0052371 A1 | 2/2021 | Singh et al. |
| 2022/0265420 A1 | 8/2022 | Kelp |

FOREIGN PATENT DOCUMENTS

| | | |
|---|---|---|
| EP | 3560457 A1 | 10/2019 |
| JP | 2010063777 B | 10/2013 |
| WO | 2014145562 A1 | 9/2014 |
| WO | 2020065516 A1 | 4/2020 |
| WO | 2020151908 A1 | 7/2020 |

* cited by examiner

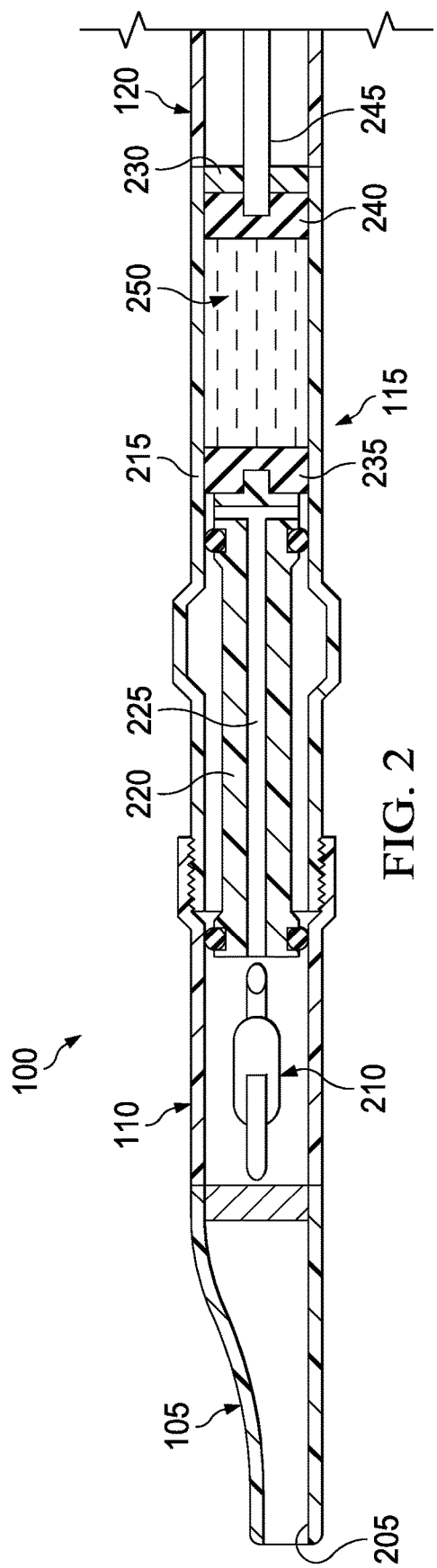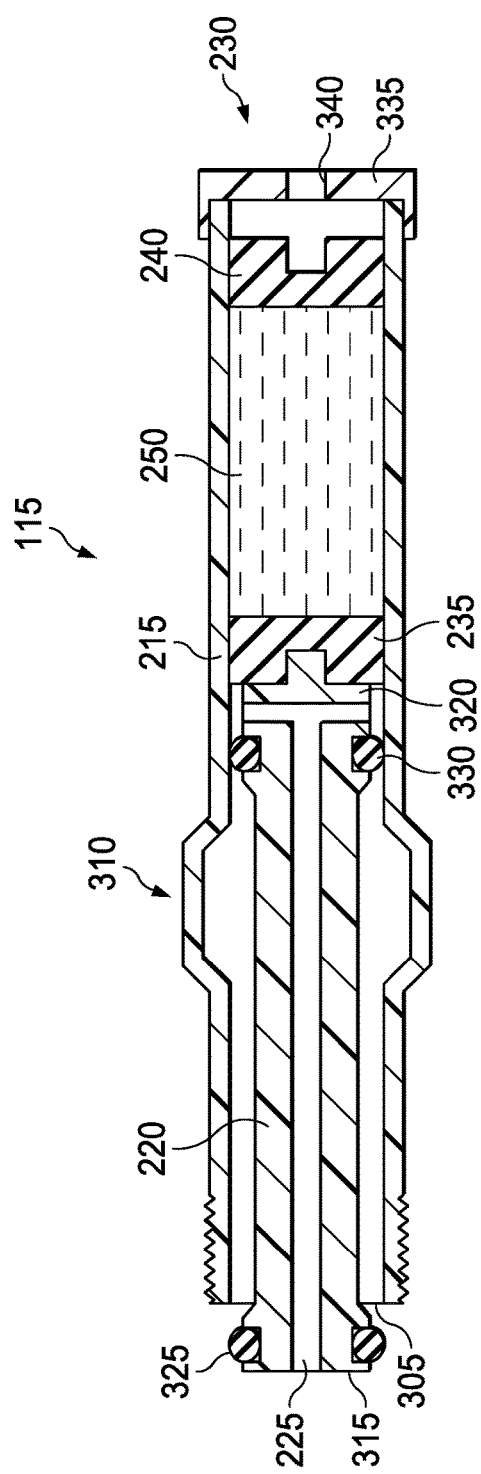

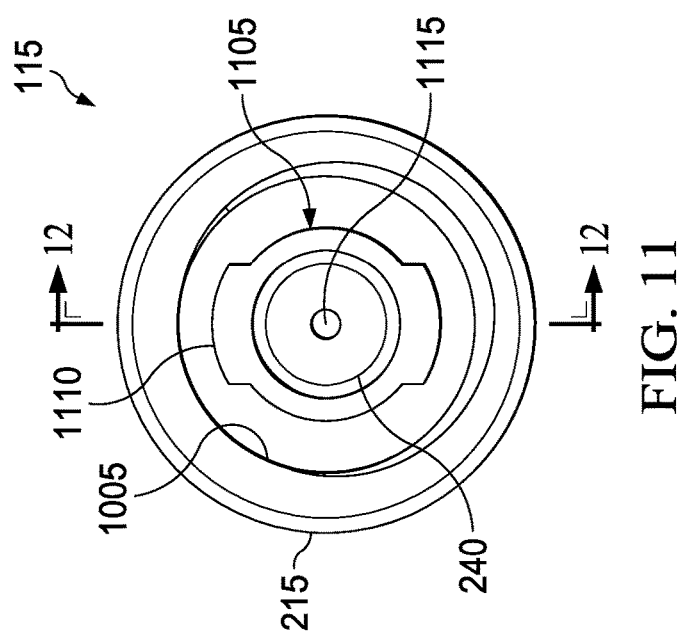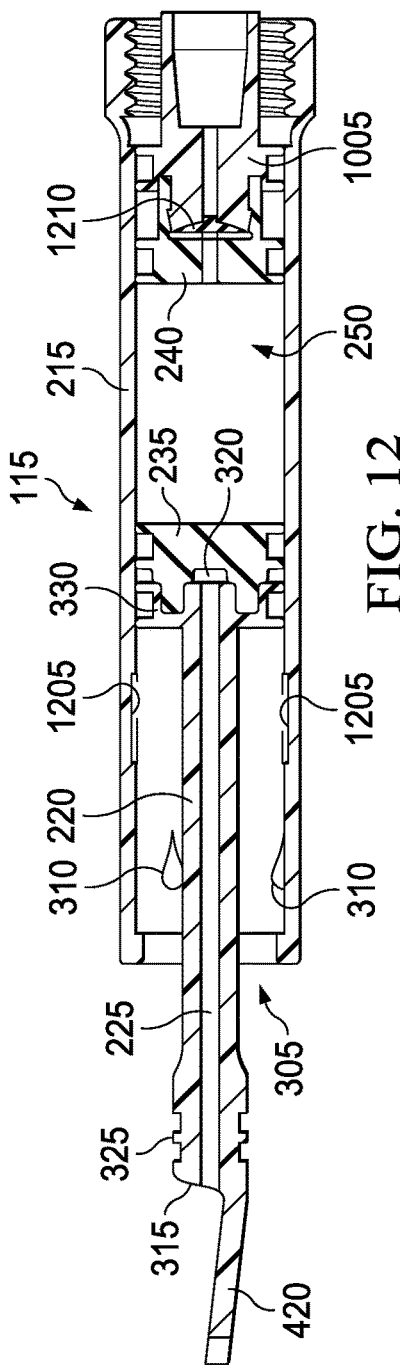

HYDRAULIC DELIVERY OF SURGICAL IMPLANTS

PRIORITY CLAIM

This application is a continuation of U.S. patent application Ser. No. 17/335,254, filed on Jun. 1, 2021, which claims the benefit of priority of U.S. Provisional Patent Application Ser. No. 63/033,258 titled "HYDRAULIC DELIVERY OF SURGICAL IMPLANTS," filed on Jun. 2, 2020, whose inventors are Todd Taber, Kathryn Jensen, Michael Piazza, Jestwin Edwin Lee, IV, Saumya Dilip Yadav, Austin Xavier Rodeheaver and Pradeep Magadum, which are hereby incorporated by reference in their entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments provide an apparatus for delivering an implant using hydraulic pressure or fluid flow. In more particular examples, an implant may be stored, advanced, and delivered to an eye using hydraulic fluid stored in a sterile container through a hollow advancement plunger. The plunger may rigidly advance the implant to a sealed position in a first phase, and then the implant may be advanced into the eye via hydraulic pressure or fluid flow in a second phase. For example, the plunger may first be used to advance the implant to a point that a seal is created about the implant within a delivery channel. The implant may then be hydraulically advanced to delivery. For example, a delivery fluid can be passed through a bore in the plunger to advance the implant. In some embodiments, an implant interface associated with the plunger may be shaped for engaging a shoulder of the implant for advancement.

Such embodiments may be particularly advantageous for delivering intraocular lenses, including accommodating lenses, which can present unique challenges for delivery. For example, an accommodating lens may contain a fluid that can be manipulated by ciliary muscle movement to change the power of the lens. Some embodiments can manage fluid in the accommodating lens to compress a relatively large lens for advancement through an acceptably small incision, manage deformation caused by shifting fluid during compression and exit from a nozzle, and execute delivery in a predictable and controlled manner. An intraocular lens may additionally include one or more haptics, which can extend radially to secure the lens within an eye. Some embodiments can reduce system complexity and the number of delivery steps while maintaining haptic position consistency. Some embodiments may also reduce the amount of working fluid for delivery.

More generally, some embodiments may provide an apparatus for advancing a lens in an implant delivery system. The apparatus may comprise a housing having a plunger interface, a drive interface, and a bypass channel disposed between the plunger interface and the drive interface. A plunger may be disposed within the housing, and the plunger may have a first end adjacent to the plunger interface, a second end, and a bore through the plunger between the first end and the second end. A plunger seal may be disposed within the housing and coupled to the second end of the plunger, and a drive seal may be disposed within the housing between the plunger seal and the drive interface. A fluid chamber may be defined within the housing between the plunger seal and the drive seal. The plunger, the plunger seal, and the drive seal are moveable in fixed relation to each other within the housing between a first position and a second position. Generally, the first end of the plunger may be configured to move through the plunger interface. In the first position, the plunger seal can fluidly isolate the bore from the fluid chamber. In the second position, the bypass channel can fluidly couple the bore to the fluid chamber around the plunger seal. In more particular embodiments, the drive seal may be movable to a third position to move fluid from the fluid chamber through the bypass channel and the bore.

Some embodiments may further comprise a nozzle seal and a bypass seal. The nozzle seal may be disposed proximate to the first end of the plunger, and the bypass seal may be configured to be disposed between the nozzle seal and the bypass channel in the second position.

Some example embodiments may additionally comprise an implant interface coupled to the first end of the plunger, which may be configured to engage a portion of an implant for advancement.

Some embodiments may additionally comprise at least one priming channel configured to fluidly couple the bore to the fluid chamber between the first position and the second position. The priming channel may have a lower flow rate than the bypass channel.

Other embodiments may provide an apparatus for implanting a lens into an eye. Such embodiments may include a nozzle having a delivery lumen, an implant bay coupled to the nozzle, and an actuator. The actuator may comprise, for example, a housing, a plunger disposed within the housing, a bore fluidly coupled to the delivery lumen through the plunger and the implant bay, a fluid chamber, and a bypass channel. The plunger may be operable to move within the housing from a first position to a second position to advance the lens from the implant bay to the delivery lumen. The bore may be fluidly isolated from the fluid chamber in the first position and can be fluidly coupled to the fluid chamber through the bypass channel in the second position. In the second position, the actuator may additionally be configured to move fluid from the fluid chamber to the delivery lumen through the bypass channel and the bore.

Other embodiments may provide a method of using a surgical delivery system. In some examples, a fluid and hydraulic plunger may be stored and transported in an actuator. The actuator may be connected to other components for storage and transport, or it may be assembled with other components to form a surgical delivery system in an operating environment. For example, in some embodiments the actuator may be connected to a drive system configured to drive the actuator. The actuator may also be connected to a nozzle configured to deliver the implant through an incision. The surgical delivery system may additionally include an implant management system configured to orient or manipulate an implant for advancement and delivery. In some examples, the drive system may push the hydraulic plunger to advance the implant into a delivery lumen of the nozzle, while a seal prevents the fluid from moving through the hydraulic plunger. The drive system may then advance the seal to allow fluid to move through a bypass channel around the seal and into the hydraulic plunger. A bore in the hydraulic plunger can carry the fluid into the delivery lumen, and the hydraulic pressure of the fluid can force the implant out of the delivery lumen.

More generally, some embodiments of a method for ejecting a lens from a surgical delivery system may include providing a lens in an implant bay, advancing the lens from the implant bay to a delivery system with a rigid plunger, and then fluidly coupling a fluid chamber to a bore in the rigid plunger through a bypass channel. Fluid in the bypass channel may then be pressed to move the fluid through the bypass channel and the bore to the delivery lumen, and the fluid may advance the lens through the delivery lumen.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

FIG. 2 is a schematic diagram of an example of the system of FIG. 1.

FIG. 3 is a detail view of an actuator that may be associated with the system of FIG. 2.

FIG. 11 is a rear view of the actuator of FIG. 10.

FIG. 12 is a section view of the actuator of FIG. 11.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
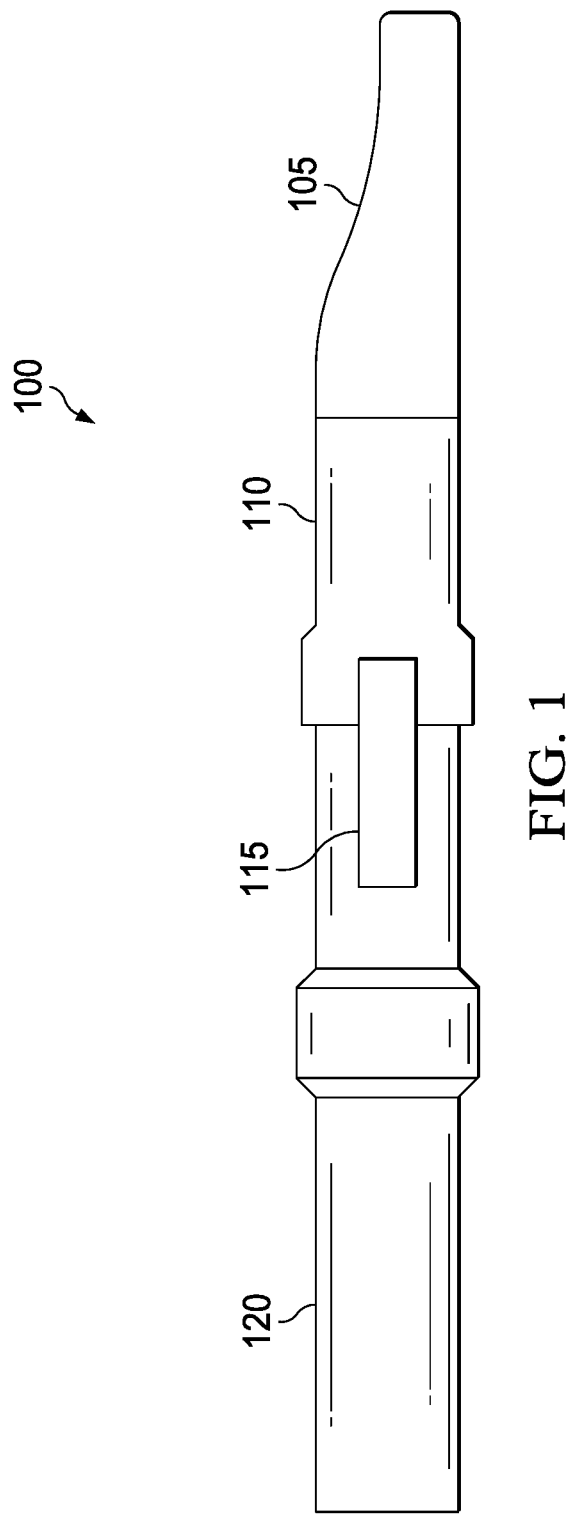
FIG. 1 is a schematic view of an example system for inserting an implant into an eye.

FIG. 1 is a schematic diagram of a system 100 that can insert an implant into an eye. In some embodiments, the system 100 may comprise two or more modules, which can be configured to be coupled and decoupled as appropriate for storage, assembly, use, and disposal. For example, as illustrated in FIG. 1, some embodiments of the system 100 may include a nozzle 105, an implant bay 110 coupled to the nozzle 105, and an actuator 115 coupled to the implant bay 110. In some embodiments, the system 100 may additionally comprise a drive module 120 configured to engage the actuator 115.

The nozzle 105 generally comprises a tip adapted for insertion through an incision into an eye. The size of the tip may be adapted to surgical requirements and techniques as needed. For example, small incisions are generally preferable to reduce or minimize healing times. Incisions of less than 3 millimeters may be preferable in some instances, and the tip of the nozzle 105 may have a width of less than 3 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may be configured to extend or splay one or more features, such as haptics, of an intraocular lens.

The actuator 115 is generally configured to advance an implant from the implant bay 110 into the nozzle 105, and thereafter from the nozzle 105 through an incision and into an eye.

The drive module 120 is generally operable to energize the actuator 115. In some examples, the drive module 120 may be operated by electrical, mechanical, hydraulic, or pneumatic power, or combinations thereof, or in some other manner. In some instances, the drive module 120 may be operated manually. According to other implementations, the drive module 120 may be an automated system.

In general, components of the system 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the actuator 115 may be mechanically coupled to the drive module 120 and may be mechanically and fluidly coupled to the implant bay 110. In some embodiments, components may also be coupled by virtue of physical proximity, being integral to a single structure, or being formed from the same piece of material.

FIG. 2 is a schematic diagram of an example of the system 100, illustrating additional details that may be associated with some embodiments. In the example of FIG. 2, the nozzle 105 has a delivery lumen 205, and an implant 210 is disposed within the implant bay 110.

The actuator 115 of FIG. 2 generally comprises a housing 215, a plunger 220 disposed within the housing 215, a bore 225 through the plunger 220, and a drive interface 230 configured to couple with the drive module 120. The plunger 220 is generally comprised of a substantially rigid material, such as a medical grade polymer material. A plunger seal 235 may be disposed within the housing 215 and coupled to the plunger 220. A drive seal 240 may also be disposed within the housing 215. In some embodiments, the drive module 120 may comprise a push rod 245 configured to engage the drive seal 240 through the drive interface 230. For example, the drive interface 230 may comprise an aperture configured to receive the push rod 245.

As illustrated in the example of FIG. 2, the drive seal 240 may be disposed between the plunger seal 235 and the drive interface 230, and a fluid chamber 250 may be defined within the housing 215 between the plunger seal 235 and the drive seal 240. In the example configuration of FIG. 2, the plunger seal 235 is configured to provide a fluid seal across the housing 215 and substantially prevent movement of fluid from the fluid chamber 250 to the bore 225. The drive seal 240 may also be configured to provide a fluid seal across the housing 215 and substantially prevent movement of fluid from the fluid chamber 250 to the drive interface 230.

FIG. 3 is a detail view of the actuator 115 of FIG. 2, illustrating additional details that may be associated with some embodiments. For example, the housing 215 of FIG. 3 further comprises a plunger interface 305 and a bypass channel 310 disposed between the plunger interface 305 and the drive interface 230. The bypass channel 310 may take various forms. For example, the bypass channel 310 may comprise a protrusion in the housing 215, as illustrated in FIG. 3. In other examples, the bypass channel 310 may comprise a groove or recess in the inner surface of the housing 215. In some embodiments, the bypass channel 310 may comprise a plurality of channels. For example, a plurality of channels may be disposed circumferentially around the housing 215 in some embodiments.

The plunger 220 generally has a first end 315 and a second end 320, wherein the first end 315 is generally disposed adjacent to the plunger interface 305. The bore 225 generally passes through the plunger 220 longitudinally from the first end 315 to the second end 320.

In some embodiments, the actuator 115 may additionally comprise a nozzle seal 325 and a bypass seal 330. Each of the nozzle seal 325 and the bypass seal 330 are generally configured to create a seal between a portion of the plunger 220 and the housing 215 to substantially prevent movement of fluid past the seal. As illustrated in the example of FIG. 3, one or both of the nozzle seal 325 and the bypass seal 330 may be ring seals, such as an O-ring, disposed circumferentially around a portion of the plunger 220. In other examples, an umbrella seal may be suitable. In more particular embodiments, the nozzle seal 325 may be disposed proximate to the first end 315 of the plunger 220, and the bypass seal 330 may be disposed proximate to the second end 320 of the plunger 220.

The drive interface 230 of FIG. 3 comprises a cap 335 and an aperture 340. The cap 335 may be coupled to an end of the housing 215 to retain the drive seal 240 and other components within the housing 215.

Figure 4:
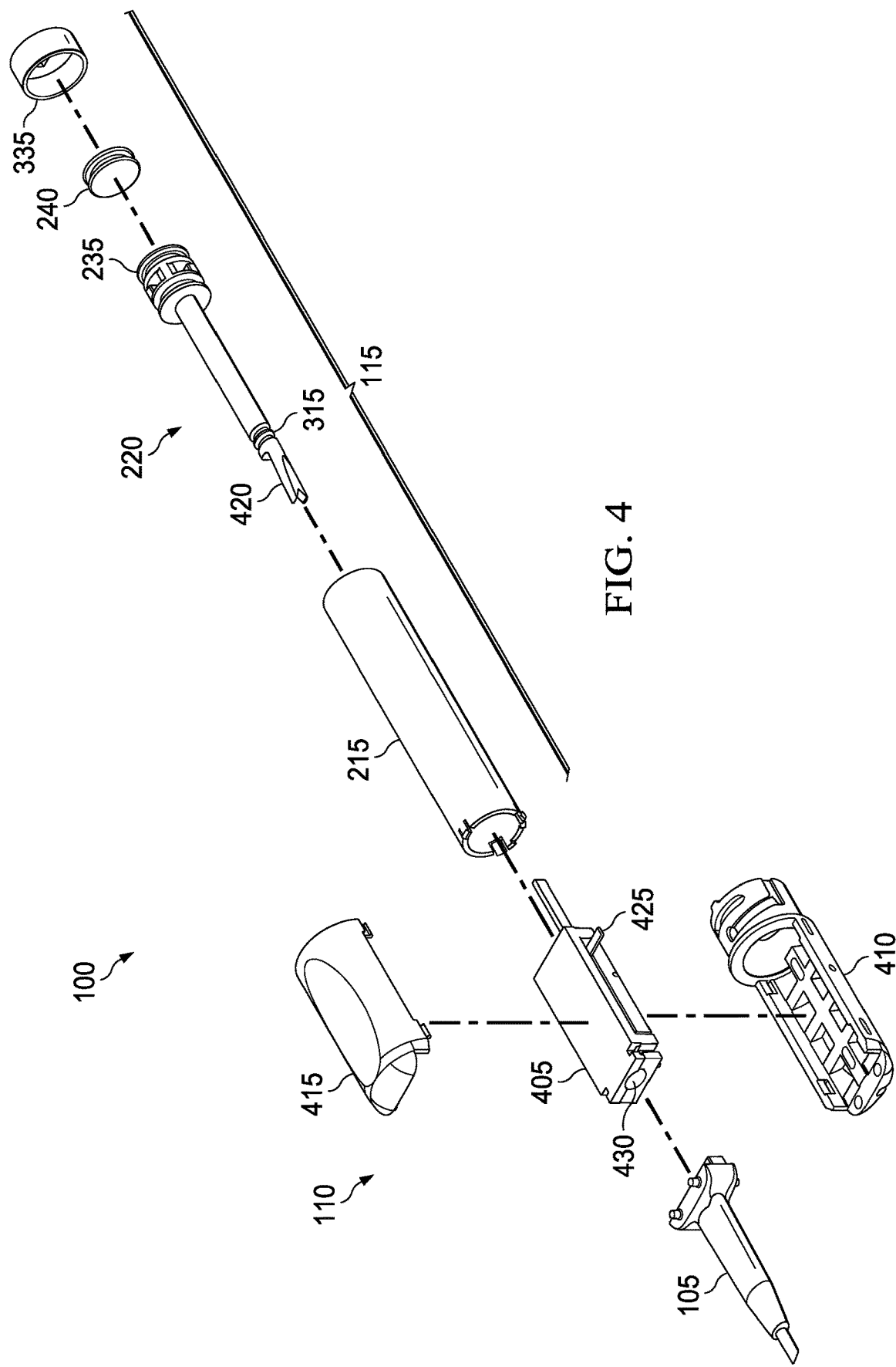
FIG. 4 is an assembly view of another example of the system of FIG. 1.

FIG. 4 is an assembly view of another example of the system 100. As illustrated in the example of FIG. 4, the implant bay 110 may comprise an implant management system 405, a base 410, and a cover 415. In various embodiments, the implant management system 405 can be any of a wide variety of systems, devices, components, or cartridges that are configured to prepare an implant for delivery. The base 410 and the cover 415 may be configured to substantially enclose the implant management system 405. The base 410 and the cover 415 may also be configured to be mechanically coupled to the nozzle 105 and to the actuator 115.

The housing 215 of FIG. 4 comprises a hollow cylinder, which can receive the plunger 220, the plunger seal 235, and the drive seal 240. FIG. 4 also illustrates an example of an implant interface 420, which may be coupled to the first end 315 of the plunger 220 in some embodiments. In the example of FIG. 4, the plunger 220 and the plunger seal 235 may be inserted into the housing 215, and then a suitable working fluid may be added before inserting the drive seal 240 and attaching the cap 335 to the housing 215.

In some examples, an implant (not shown) may be preloaded into the implant management system 405. The implant management system 405 is generally configured to store and manipulate an implant. For example, some embodiments of the implant management system 405 may be configured to orient or fold an implant. In some particular instances, the implant management system 405 may be configured to fold, splay, or straighten haptics of an intraocular lens. In the example of FIG. 4, the implant management system 405 comprises an arm 425, which may be operable to manipulate an implant within an implant chamber 430. Other examples may additionally or alternatively comprise other suitable mechanisms for manipulating the arm 425, such as a rotating dial, cap, or wheel. In the example of FIG. 4, the arm 425 is configured to accept a user actuation of the implant management system 405.

Figure 5:
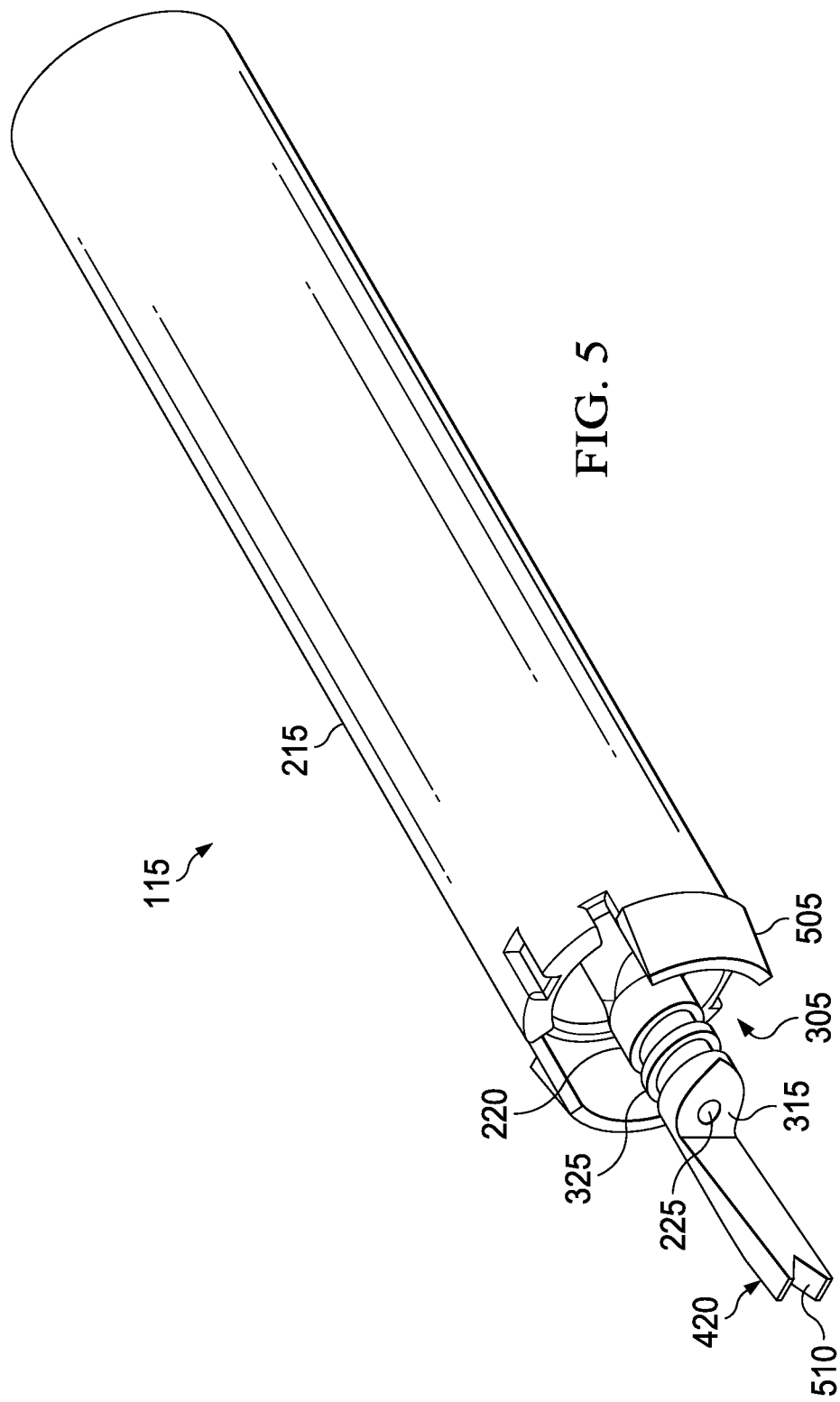
FIG. 5 is an isometric view of an actuator illustrated in FIG. 4.

FIG. 5 is an isometric view of the actuator 115 of FIG. 4, as assembled. As illustrated in the example of FIG. 5, some embodiments of the plunger interface 305 may comprise an opening in the housing 215 and one or more locking tabs 505. The implant interface 420 and at least a portion of the plunger 220 may extend through the plunger interface 305. The nozzle seal 325 of FIG. 5 comprises an O-ring disposed around the plunger 220 adjacent to the first end 315. As seen in the example of FIG. 5, the bore 225 may define an opening in the first end 315. In some embodiments, the opening may be centrally disposed through the first end 315, and the implant interface 420 may be coupled to the plunger 220 adjacent to the opening in the first end 315. The implant interface 420 may comprise a notch 510, which may be configured to engage an implant.

Figure 6:
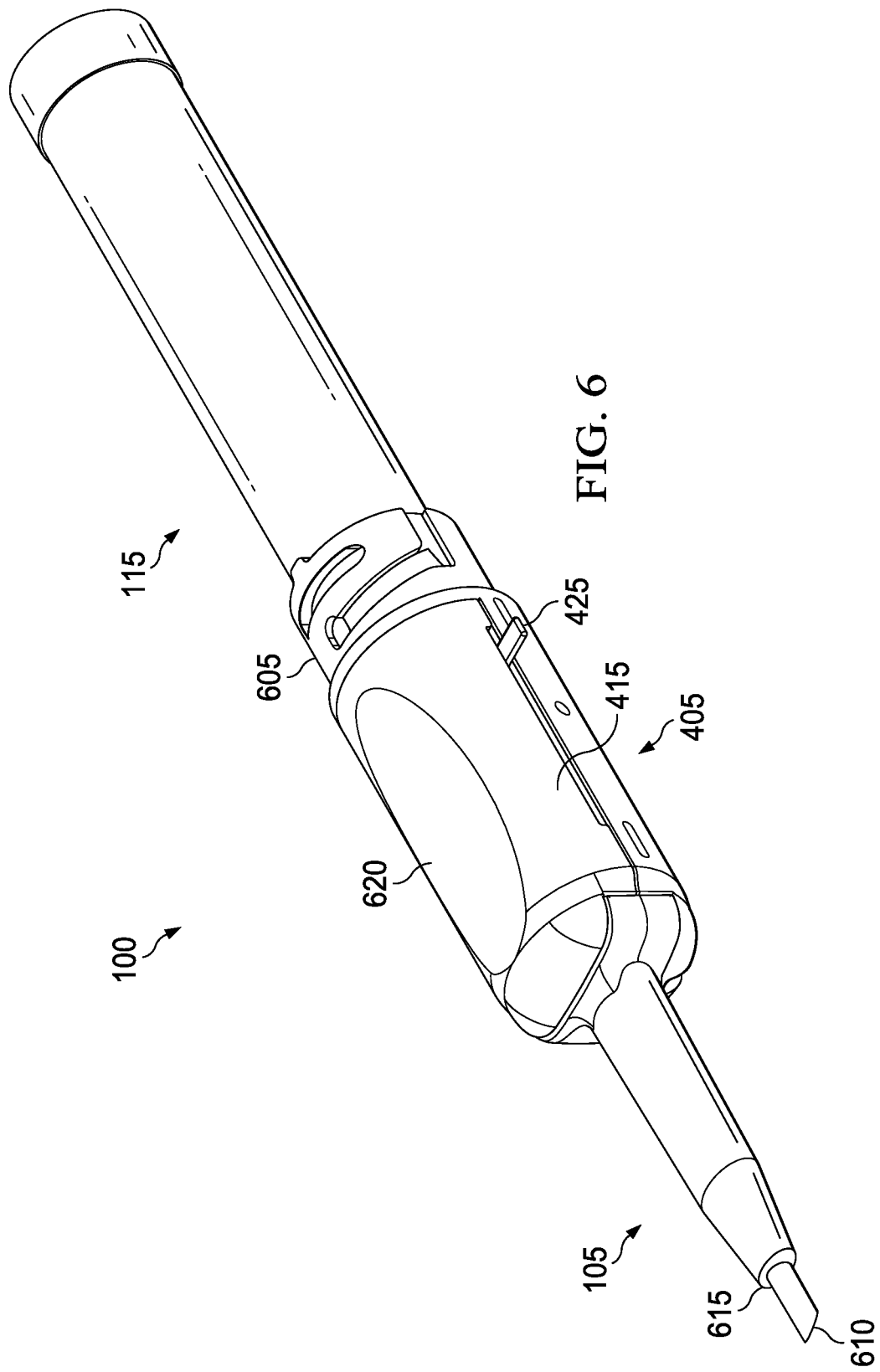
FIG. 6 is an isometric view of the system of FIG. 4, as assembled.

FIG. 6 is an isometric view of the system 100 of FIG. 4 as assembled, illustrating additional details that may be associated with some embodiments. As illustrated in the example of FIG. 6, the system 100 may have a slender, elongated shape. In some instances, the actuator 115 may be at least partially inserted into the implant bay 110 and secured in position by a locking mechanism 605 adapted to engage interlocking features of the actuator 115, such as the locking tabs 505. In other examples, the actuator 115 may be secured by other suitable fasteners, interference fit, or thermal or chemical bonding.

As illustrated in the example of FIG. 6, some embodiments of the nozzle 105 may comprise an insertion tip 610 and an incision guard 615. The insertion tip 610 may be adapted to minimize shear forces on an incision. In some examples, the insertion tip 610 may be beveled or angled. The incision guard 615 may comprise a flared portion adapted to contact the eye around the incision to limit the penetration depth of the insertion tip 610.

Some embodiments of the system 100 may additionally include various ergonomic features. In FIG. 6, for example, the cover 415 of the implant management system 405 includes a relief 620. The relief 620 of FIG. 6 comprises a shallow recess formed in the cover 415 to accommodate, for example, one or more fingers of an operator. The relief 620 may additionally include a textured surface that may improve grip of and control over the system 100.

Figure 7:
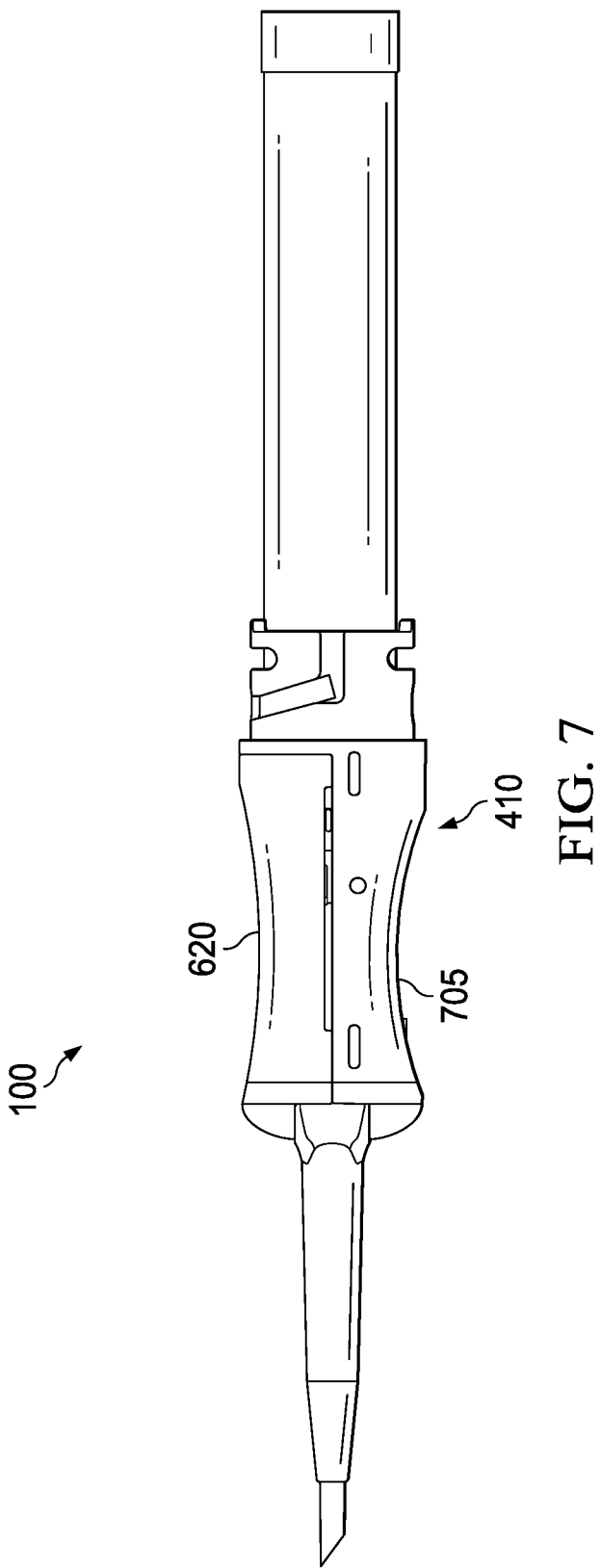
FIG. 7 is a side view of the system of FIG. 6.

FIG. 7 is a side view of the system 100 of FIG. 6, illustrating additional details that may be associated with some embodiments. As illustrated in the example of FIG. 7, the base 410 may comprise a relief 705, similar or analogous to the relief 620.

Figure 8:
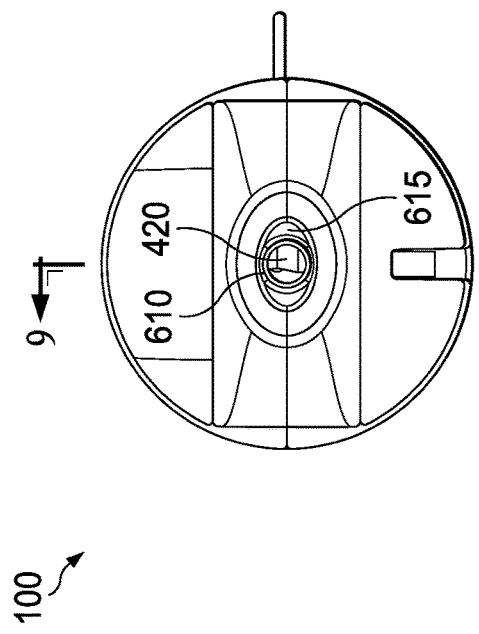
FIG. 8 is a front view of the system of FIG. 6.

FIG. 8 is a front view of the system 100 of FIG. 6. As illustrated in FIG. 8, the insertion tip 610 may have a circular profile, and the incision guard 615 may have an elliptical profile. The insertion tip 610 and the incision guard 615 may be concentric in some embodiments, as illustrated in the example of FIG. 8.

Figure 9:
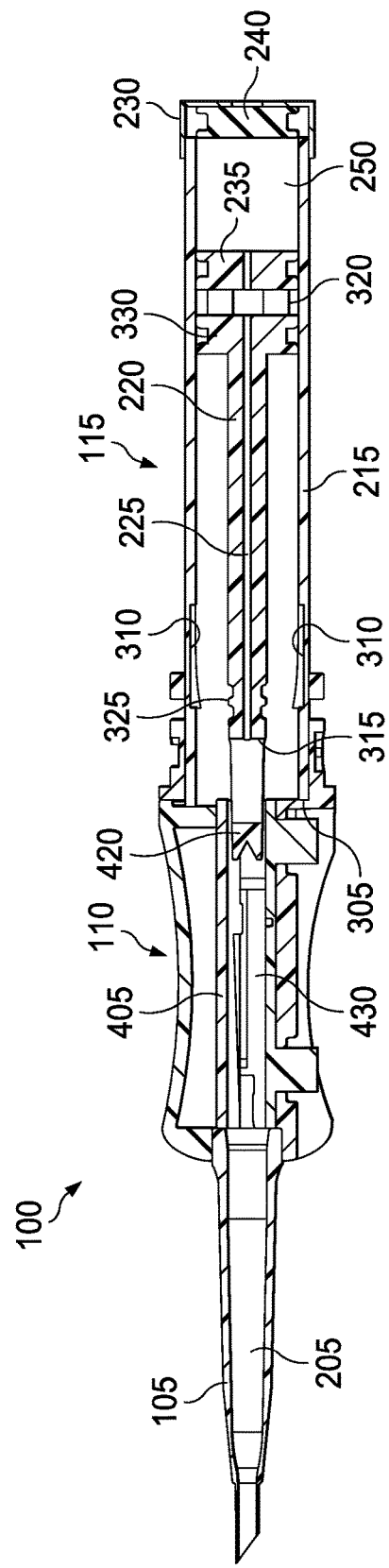
FIG. 9 is a section view of the system of FIG. 8.

FIG. 9 is a section view of the system 100 of FIG. 8 taken along line 9-9, illustrating additional details that may be associated with some embodiments. In the example of FIG. 9, the nozzle 105 is coupled to the implant bay 110, and the actuator 115 is coupled to the implant bay 110. The plunger 220 is disposed within the housing 215, and the bore 225 extends through the plunger 220 between the first end 315 and the second end 320. The plunger seal 235 may be disposed within the housing 215 and coupled to the second end 320 of the plunger 220.

The drive seal 240 may be disposed between the plunger seal 235 and the drive interface 230, and the fluid chamber 250 may be defined within the housing 215 between the plunger seal 235 and the drive seal 240. In the example configuration of FIG. 9, the plunger seal 235 is configured to provide a fluid seal across the housing 215 and substantially prevent movement of fluid from the fluid chamber 250 to the bore 225. The drive seal 240 may also be configured to provide a fluid seal across the housing 215 and substantially prevent movement of fluid from the fluid chamber 250 to the drive interface 230.

The bypass channel 310 may be disposed between the plunger interface 305 and the drive interface 230. The bypass channel 310 of FIG. 9 comprises a recess in the inner surface of the housing 215.

If assembled as illustrated in FIG. 9, the implant chamber 430 may provide a fluid path between the bore 225 and the delivery lumen 205. The implant chamber 430 may also be configured to receive a portion of the plunger 220, including the implant interface 420 in some embodiments.

The example configuration of FIG. 9 is generally suitable for storing an implant (not shown) before delivery. More particularly, the plunger seal 235, and the drive seal 240 can be disposed in a first position, wherein the plunger seal 235 fluidly isolates the bore 225 and the bypass channel 310 from the fluid chamber 250, allowing a suitable working fluid to be stored in the fluid chamber 250. Suitable working fluids may include, without limitation, a liquid, such as saline, or a viscous lubricant with non-Newtonian properties.

Figure 10:
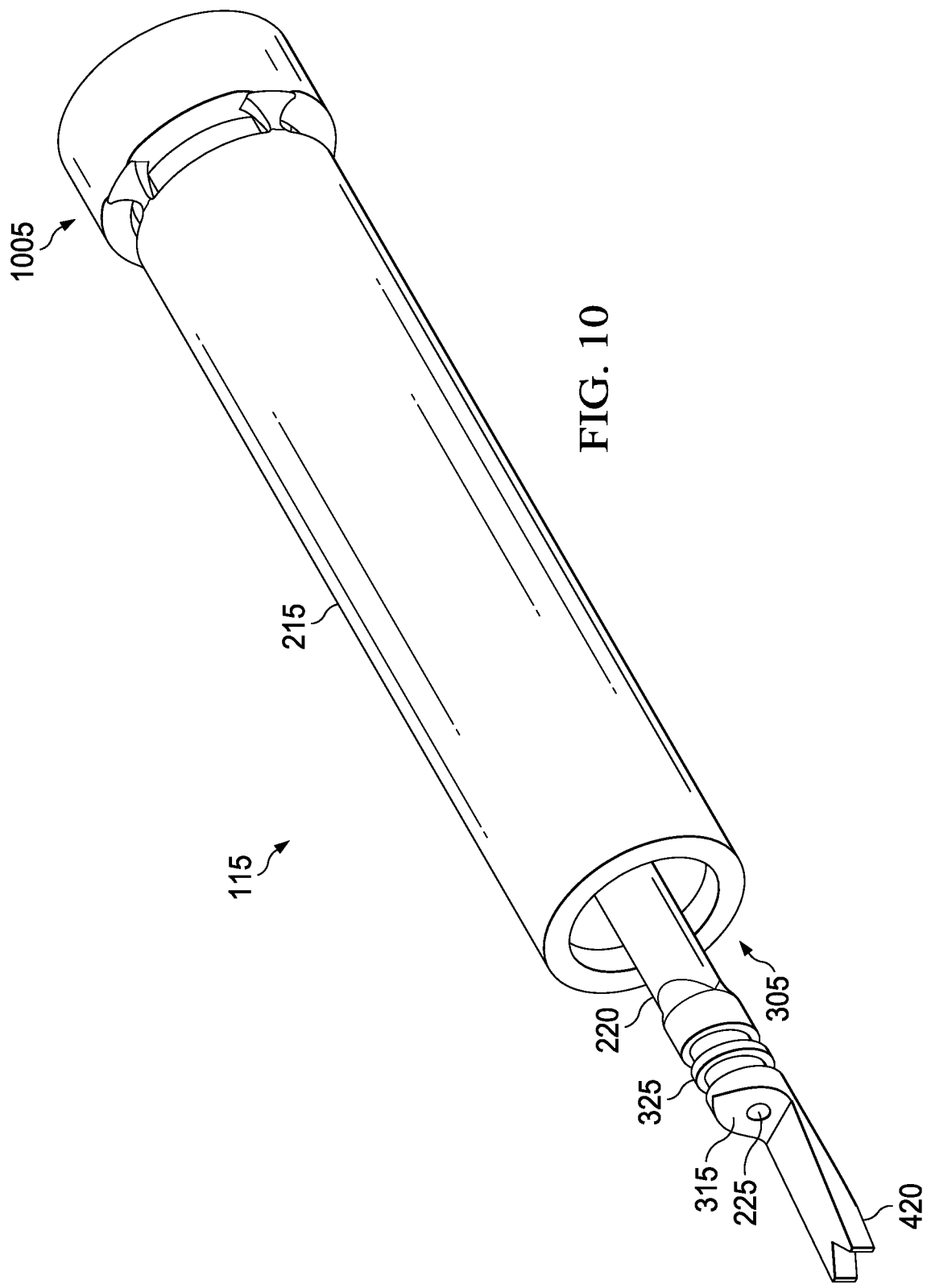
FIG. 10 is an isometric view of another example of an actuator that may be associated with the system of FIG. 1.

FIG. 10 is an isometric view of another example of the actuator 115, illustrating additional details that may be associated with some embodiments. The actuator 115 of FIG. 10 is similar to the actuator 115 of FIG. 5. For example, the plunger interface 305 of FIG. 10 may comprise an opening in the housing 215, and the implant interface 420 and at least a portion of the plunger 220 may extend through the plunger interface 305. The nozzle seal 325 of FIG. 10 comprises an O-ring disposed around the plunger 220 adjacent to the first end 315. As seen in the example of FIG. 10, the bore 225 may define an opening in the first end 315. In some embodiments, the opening may be centrally disposed through the first end 315, and the implant interface 420 may be coupled to the plunger 220 adjacent to the opening in the first end 315. The actuator 115 of FIG. 10 further comprises a fluid fitting 1005.

FIG. 11 is a rear view of the actuator 115 of FIG. 10, illustrating additional details that may be associated with some embodiments of the fluid fitting 1005. In the example of FIG. 11, at least a portion of the fluid fitting 1005 may be integral with the housing 215. The fluid fitting 1005 may be a luer lock, luer slip, or similar fitting configured to receive a syringe or other apparatus. For example, the fluid fitting 1005 of FIG. 11 comprises a female luer lock 1105 having at least one locking tab 1110 configured to engage threads on a compatible male luer lock fitting. A port 1115 may be disposed in the drive seal 240 of the female luer lock 1105.

FIG. 12 is a section view of the actuator 115 of FIG. 11 taken along line 12-12. In the example of FIG. 12, the plunger 220 is disposed within the housing 215, and the bore 225 extends through the plunger 220 between the first end 315 and the second end 320. The plunger seal 235 may be disposed within the housing 215 and coupled to the second end 320 of the plunger 220. The implant interface 420 may be coupled to the first end 315 in some embodiments of the plunger 220.

The drive seal 240 may be integral to or coupled to the fluid fitting 1005, and the fluid chamber 250 may be defined within the housing 215 between the plunger seal 235 and the drive seal 240. In the example configuration of FIG. 12, the plunger seal 235 is configured to provide a fluid seal across the housing 215 and substantially prevent movement of fluid between the bore 225 and the fluid chamber 250. The drive seal 240 may also be configured to provide a fluid seal across the housing 215 and substantially prevent movement of fluid between the drive interface 230 and the fluid chamber 250.

The bypass channel 310 may be disposed between the plunger interface 305 and the drive seal 240. In more particular embodiments, the bypass channel 310 may be disposed between the plunger interface 305 and the plunger seal 235. The bypass channel 310 of FIG. 12 comprises a recess in the inner surface of the housing 215. In some examples, the bypass channel 310 may have a width that that increases with distance from the plunger seal 235.

As illustrated in the example of FIG. 12, some embodiments of the actuator 115 may optionally have at least one priming channel 1205. The priming channel 1205 may take various forms. For example, the priming channel 1205 may comprise a groove or recess in the inner surface of the housing 215, as illustrated in the example of FIG. 12. In other examples, the priming channel 1205 may comprise a protrusion in the housing 215. In some embodiments, the priming channel 1205 may comprise a plurality of channels. For example, a plurality of channels may be disposed circumferentially around the housing 215 in some embodiments.

In the example of FIG. 12, the nozzle seal 325 is disposed proximate to the first end 315 of the plunger 220, and the bypass seal 330 is disposed proximate to the second end 320 of the plunger 220.

As illustrated in FIG. 12, the port 1115 may comprise a fill seal 1210. The fill seal 1210 may comprise a self-sealing material adapted to allow penetration of a fluid while sealing upon removal. For example, the actuator 115 of FIG. 12 may be transported and stored without fluid in the fluid chamber 250. A syringe or other suitable fluid source (not shown) may then be coupled to the fluid fitting 1105 through the port 1115 and the fill seal 1210 to add a suitable working fluid to the fluid chamber 250. Additionally, or alternatively, a check valve or umbrella valve may be configured to allow fluid to pass into the fluid chamber 250 and prevent backflow.

Figure 13A:
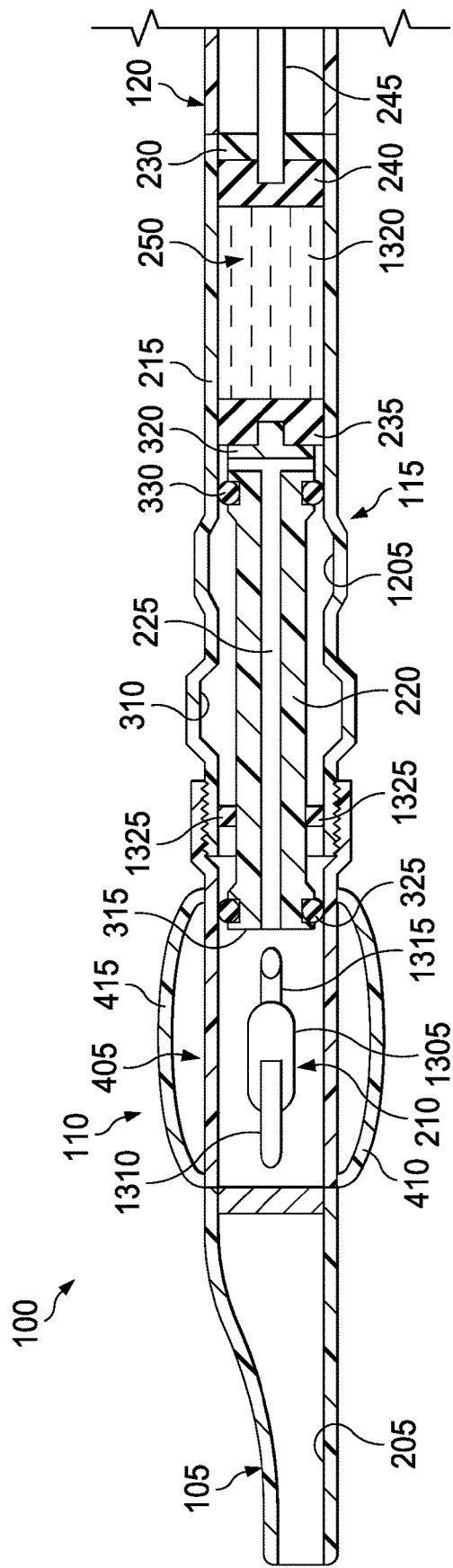
FIGS. 13A-13D are schematic diagrams illustrating an example method of ejecting an implant from the system of FIG. 1.

FIGS. 13A-13D are schematic diagrams illustrating an example method of ejecting the implant 210 from the system 100. Initially, various components of the system may be assembled if needed. For example, the nozzle 105, the implant bay 110, and the actuator 115 may be coupled to each other as illustrated in FIG. 13A. The drive system 120 may also be coupled to the actuator 115 through the drive interface 230. For example, the push rod 245 may engage the drive seal 240 through the drive interface 230 as illustrated in FIG. 13A.

The implant 210 may be provided in the implant management system 405 of the implant bay 110, as illustrated in the example of FIG. 13A. In some embodiments, the implant 210 may comprise an intraocular lens having an optic 1305, a leading haptic 1310, and a trailing haptic 1315. An intraocular lens may have a shape similar to that of a natural lens of an eye, and it may be made from numerous materials. Examples of suitable materials may include silicone, acrylic, and combinations of such suitable materials. In some instances, the implant 210 may comprise an intraocular lens that is fluid-filled, such as a fluid-filled accommodating intraocular lens.

In some examples, a working fluid 1320 may be stored in the fluid chamber 250. In other examples, such as the embodiment of FIG. 10, the working fluid 1320 may be added to the fluid chamber 250 at any time before use.

Figure 13B:
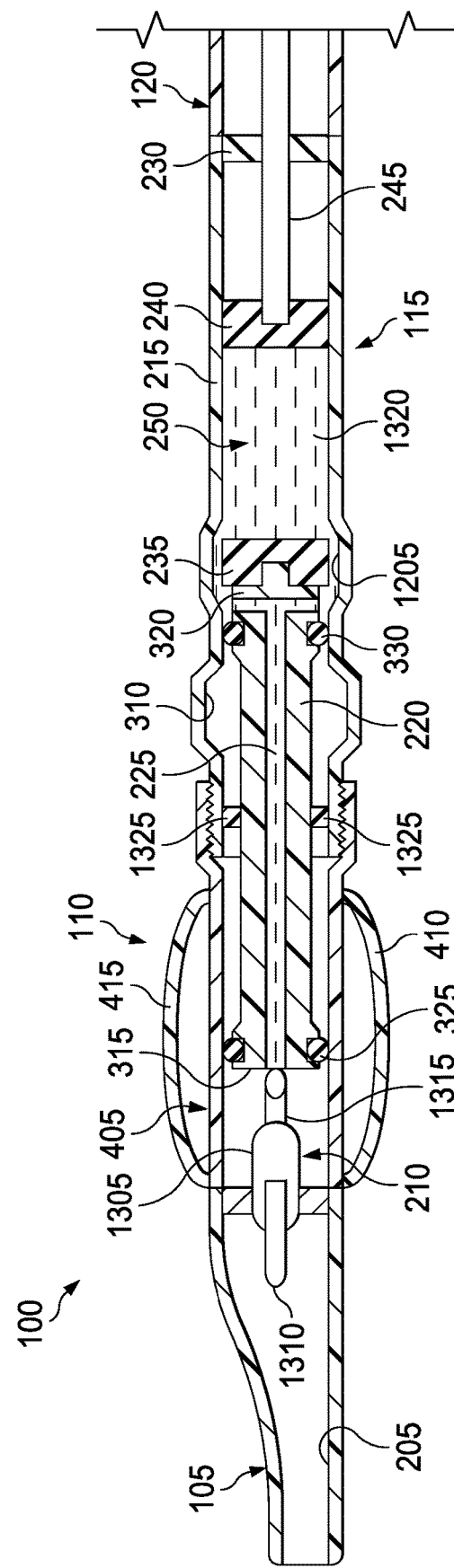
Figure 13C:
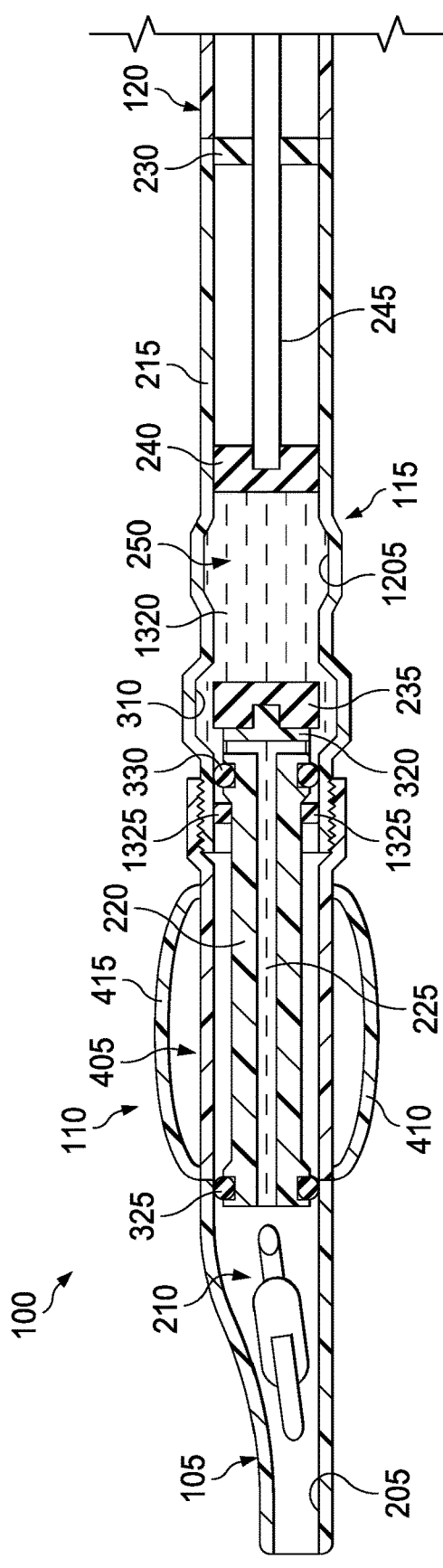
Figure 13D:
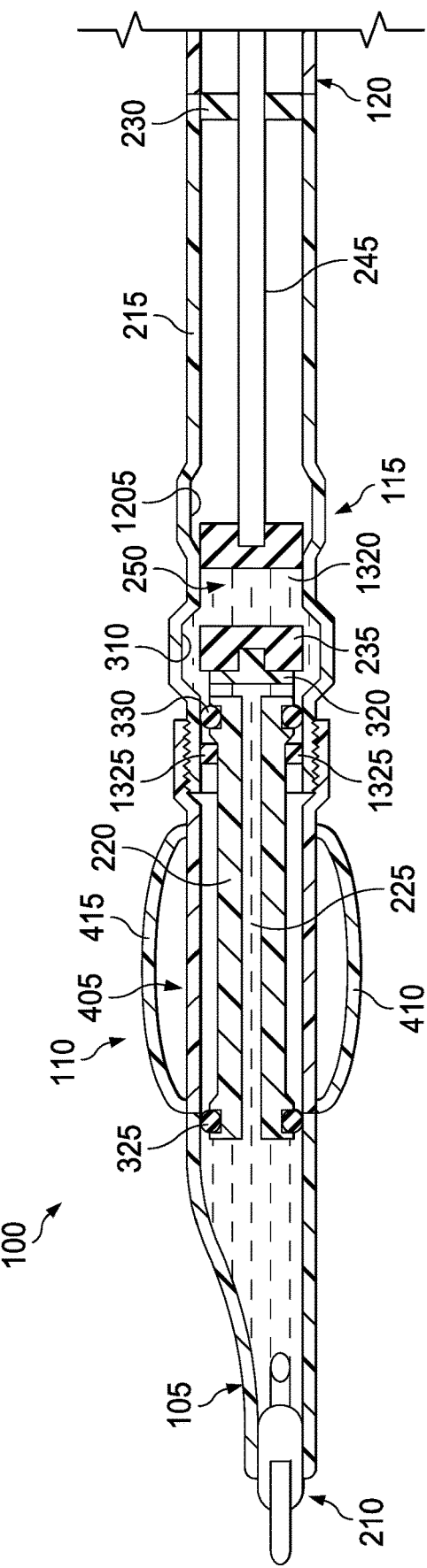

The plunger 220, the plunger seal 235, and the drive seal 240 are generally movable within the housing between a first position, as illustrated in the example of FIG. 13A, and other positions illustrated in FIG. 13B-13D.

In the first position of FIG. 13A, the plunger seal 235 fluidly isolates the bore 225 from the working fluid 1320 in the fluid chamber 250, which can allow the working fluid 1320 to be stored within the fluid chamber 250 in the first position. In some examples, the nozzle seal 325 and the first end 315 of the plunger 220 may protrude into the implant bay 110 in the first position, as illustrated in FIG. 13A, which can create a seal in the implant bay 110 behind the implant 210. The first end 315 of the plunger 220 may also engage the implant 210 in the first position, in some examples. In other examples, the nozzle seal 325 and the first end 315 may be contained within the housing 215 in the first position.

In some embodiments, the implant management system 405 may be actuated to configure the implant 210 for delivery. For example, the implant management system 405 may straighten one or more of the leading haptic 1310 and the trailing haptic 1315.

In some embodiments, the drive system 120 may move the push rod 245 against the drive seal 240. The plunger 220, the plunger seal 235, the drive seal 240, and the working fluid 1320 can rigidly move to a second position, maintaining a fixed relationship as illustrated in FIG. 13B, in response to the force of the push rod 245 on the drive seal 240. In the example of FIG. 13B, the implant 210 is also advanced partially into the delivery lumen 205 of the nozzle 105 by the first end 315 of the plunger 220. For example, the first end 315 may engage the optic 1305 in some embodiments. Advancement may also passively straighten the trailing haptic 1315 in some embodiments. In the second position of FIG. 13B, the plunger seal 235 is advanced to a position adjacent to the priming channel 1205. The priming channel 1205 fluidly couples the fluid chamber 250 to the bore 225 around the plunger seal 235. As the push rod 245 and the drive seal 240 apply pressure to the working fluid 1320 in the fluid chamber 250, the working fluid 1320 may move into the bore 225 through the priming channel 1205.

In general, the rate of fluid flow through the priming channel 1205 is sufficiently low and brief to minimize bubble formation in the fluid and to maintain a pressure in the working fluid 1320 sufficient to continue advancement of the plunger seal 235 and the plunger 220 to a third position, as illustrated in FIG. 13C, in response to pressure applied to the drive seal 240 by the push rod 245. In the position of FIG. 13C, the implant 210 is advanced further into the delivery lumen 205, which may create a fluid seal between the implant 210 and the delivery lumen 205. In some examples, the implant 210 may be positioned entirely within the delivery lumen 205. In the third position, the bypass channel 310 fluidly couples the bore 225 to the fluid chamber 250 around the plunger seal 235. As the push rod 245 and the drive seal 240 apply pressure to the working fluid 1320 in the fluid chamber 250, the working fluid 1320 may move into the bore 225 through the bypass channel 310, unimpeded at a higher flow rate.

The plunger 220 may be retained in the third position of FIG. 13C against further force applied to the drive seal 240. For example, in some embodiments, the second end 320 of the plunger 220 may be flared, and the plunger interface 305 may be configured to engage the second end 320 to limit advancement. Additionally, or alternatively, the implant bay 110 or the nozzle 105 may comprise a plunger stop 1325 configured to engage some portion or feature of the plunger 220, such as the second end 320 of the plunger 220, to prevent further advancement. In yet other examples, some embodiments of the delivery lumen 205 may be tapered, which can prevent further advancement of the plunger 220 toward the insertion tip 615. For example, the diameter of the delivery lumen 205 may decrease as it gets closer to the insertion tip 615.

With the plunger 220 retained, additional pressure applied by the drive seal 240 on the working fluid 1320 can move the working fluid 1320 through the bypass channel 310 and the bore 225, as illustrated in the example of FIG. 13D. Movement of the working fluid 1320 from the bore 225 into the delivery lumen 205 under pressure from the drive seal 240 can increase the pressure and flow rate of the working fluid 1320 in the delivery lumen 205 behind the implant 210, which can advance the implant 210 further through the delivery lumen 205 until the implant 210 is ejected.

Figure 14A:
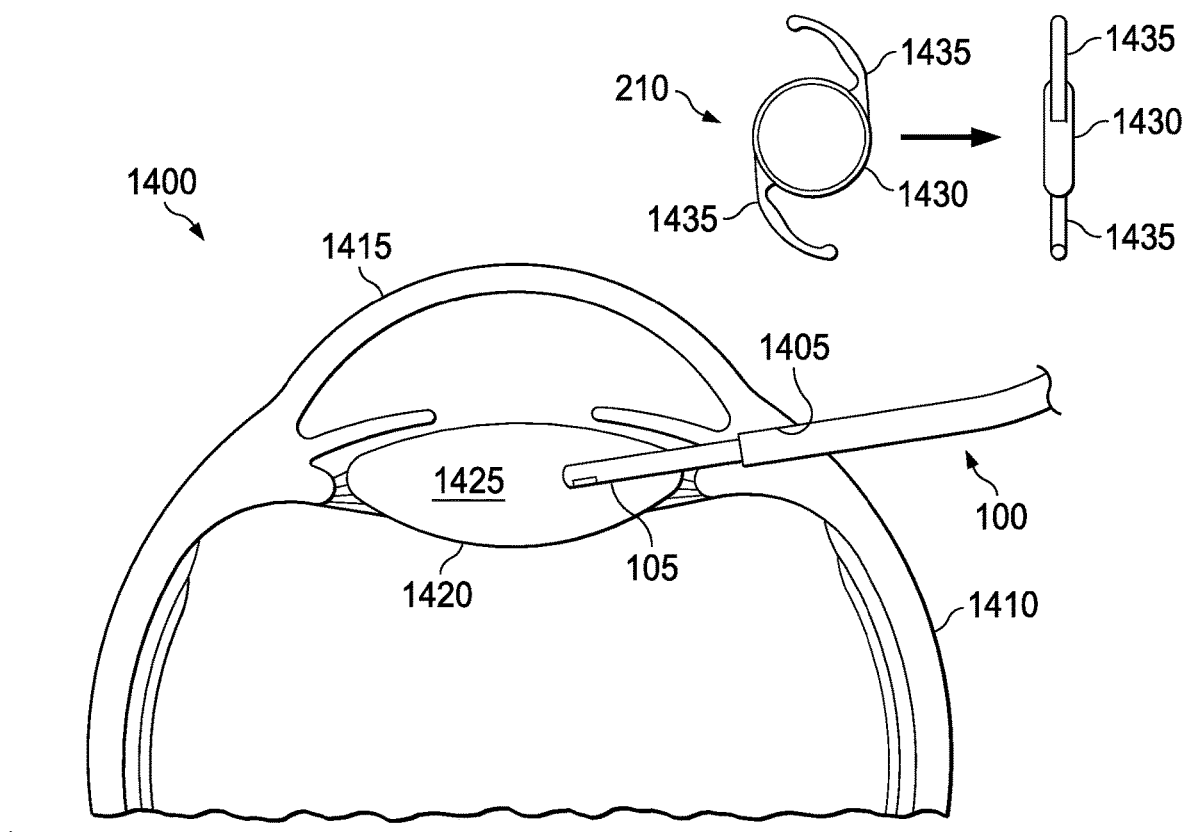
FIG. 14A-14B are schematic diagrams illustrating an example application of the system of FIG. 1 to insert an implant into an eye.
Figure 14B:
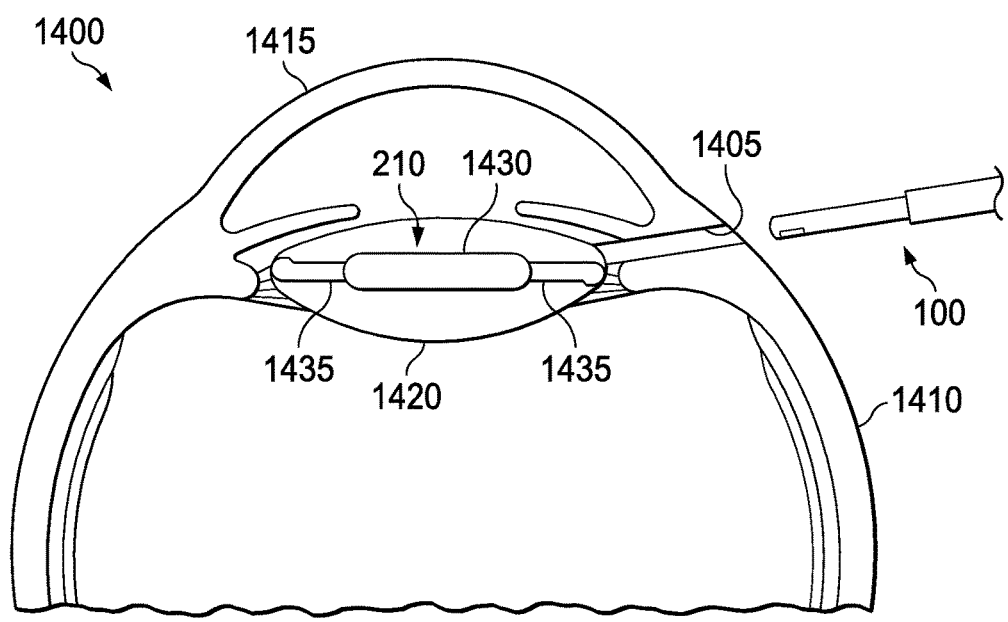

FIGS. 14A-14B are schematic diagrams further illustrating an example use of the system 100 to deliver the implant 210 to an eye 1400. As illustrated, an incision 1405 may be made in the eye 1400 by a surgeon, for example. In some instances, the incision 1405 may be made through the sclera 1410 of the eye 1400. In other instances, an incision may be formed in the cornea 1415 of the eye 1400. The incision 1405 may be sized to permit insertion of a portion of the nozzle 105 in order to deliver the implant 210 into the capsular bag 1420. For example, in some instances, the size of the incision 1405 may have a length less than about 3000 microns (3 millimeters). In other instances, the incision 1405 may have a length of from about 1000 microns to about 1500 microns, from about 1500 microns to about 2000 microns, from about 2000 microns to about 2500 microns, or from about 2500 microns to about 3000 microns.

After the incision 1405 is made, the nozzle 105 can be inserted through the incision 1405 into an interior portion 1425 of the eye 1400. The system 100 can then eject the implant 210 through the nozzle 105 into the capsular bag 1420 of the eye 1400. In some applications, the implant 210 may be delivered in a folded configuration and can revert to an initial, unfolded state, within the capsular bag 1420, as shown in FIG. 14B. In the example of FIG. 14B, the implant 210 is illustrative of an intraocular lens having an optic 1430 and haptics 1435. For example, the implant 210 may be in the form of an accommodating intraocular lense having the optic 1430 and/or haptics 1435 filled with fluid. The capsular bag 1420 can retain the implant 210 within the eye 1400 in a relationship relative to the eye 1400 so that the optic 1430 refracts light directed to the retina (not shown). The haptics 1435 can engage the capsular bag 1420 to secure the implant 210 therein. After dispensing the implant 210 into the capsular bag 1420, the nozzle 105 may be removed from the eye 1400 through the incision 1405, and the eye 1400 is allowed to heal over a period of time.

The systems, apparatuses, and methods described herein may provide significant advantages. For example, some embodiments may be particularly advantageous for delivering intraocular lenses, including fluid-filled accommodating lenses, which can present unique challenges for delivery. Some embodiments can compress a relatively large lens to fit through an acceptably small incision, manage deformation caused by shifting fluid during compression and exit from a nozzle, and execute delivery in a predictable and controlled manner. Additionally, some embodiments can reduce system complexity and the number of delivery steps while maintaining haptic position consistency. Some embodiments may also reduce the amount of working fluid for delivery.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations, the nozzle 105, the implant bay 110, the actuator 115, the drive system 120 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for advancing a lens in an implant delivery system, the apparatus comprising:
    a housing comprising a fluid chamber and a bypass channel; and
    a plunger disposed within the housing, the plunger having a first end, a second end, and a bore between the first end and the second end;
    wherein the plunger is movable within the housing between a first position in which the bore is fluidly isolated from the fluid chamber and a second position in which the bypass channel fluidly couples the bore to the fluid chamber.

2. The apparatus of claim 1, further comprising a drive seal configured to move fluid from the fluid chamber through the bypass channel and the bore in the second position.

3. The apparatus of claim 1, further comprising:
    a nozzle seal disposed proximate to the first end of the plunger; and
    a bypass seal configured to be disposed between the nozzle seal and the bypass channel in the second position.

4. The apparatus of claim 1, further comprising a lens interface coupled to the first end of the plunger.

5. The apparatus of claim 1, wherein the bypass channel comprises a plurality of channels disposed circumferentially around the housing.

6. The apparatus of claim 1, further comprising a priming channel configured to fluidly couple the bore to the fluid chamber between the first position and the second position.

7. The apparatus of claim 6, wherein the priming channel has a lower flow rate than the bypass channel.

8. An apparatus for implanting a lens into an eye, the apparatus comprising:
    a nozzle having a delivery lumen;
    an implant bay coupled to the nozzle;
    a fluid chamber;
    a bypass channel;
    a plunger having a first end, a second end, and a bore between the first end and the second end; and
    a drive seal;
    wherein the plunger is movable between a first position and a second position to advance the lens from the implant bay to the delivery lumen, the bore being fluidly isolated from the fluid chamber in the first position and fluidly coupled to the fluid chamber through the bypass channel in the second position, and the drive seal is configured to move fluid from the fluid chamber through the bypass channel and the bore in the second position to advance the lens through the delivery lumen.

9. The apparatus of claim 8, further comprising a lens interface coupled to first end of the plunger.

10. The apparatus of claim 8, further comprising a priming channel configured to fluidly couple the bore to the fluid chamber between the first position and the second position.

11. The apparatus of claim 10, wherein the priming channel has a lower flow rate than the bypass channel.

12. The apparatus of claim 8, further comprising a drive interface configured to receive a push rod for engaging the drive seal.

13. The apparatus of claim 8, further comprising a fluid disposed in the fluid chamber.

14. The apparatus of claim 8, further comprising:
a drive interface; and
a push rod configured to engage the drive seal through the drive interface.

15. An apparatus for implanting a lens into an eye, the apparatus comprising:
a nozzle having a delivery lumen;
an implant bay coupled to the nozzle;
a fluid chamber;
a bypass channel;
a plunger having a first end, a second end, and a bore between the first end and the second end, the plunger movable between a first position and a second position;
a drive seal;
a nozzle seal disposed proximate to the first end of the plunger; and
a bypass seal configured to be disposed between the nozzle seal and the bypass channel in the second position;
wherein moving the plunger from the first position to the second position advances the lens from the implant bay to the delivery lumen, the bore being fluidly isolated from the fluid chamber in the first position and fluidly coupled to the fluid chamber through the bypass channel in the second position, and the drive seal is configured to move fluid from the fluid chamber through the bypass channel and the bore in the second position to advance the lens through the delivery lumen.

16. An apparatus for implanting a lens into an eye, the apparatus comprising:
a nozzle having a delivery lumen;
an implant bay coupled to the nozzle;
a fluid chamber;
a housing comprising a bypass channel, the bypass channel comprising a plurality of channels disposed circumferentially around the housing;
a plunger having a first end, a second end, and a bore between the first end and the second end; and
a drive seal;
wherein the plunger is movable between a first position and a second position to advance the lens from the implant bay to the delivery lumen, the bore being fluidly isolated from the fluid chamber in the first position and fluidly coupled to the fluid chamber through the bypass channel in the second position, and the drive seal is configured to move fluid from the fluid chamber through the bypass channel and the bore in the second position to advance the lens through the delivery lumen.

* * * * *